United States Patent [19]

Paxton et al.

[11] Patent Number: 4,472,404

[45] Date of Patent: Sep. 18, 1984

[54] 8-QUINOLINYL CARBAMATES AND THEIR USE AS URINARY TRACT ANTIMICROBIALS

[75] Inventors: Larry D. Paxton, Rochester, N.Y.; Rita A. Madison; Joseph E. Dunbar, both of Midland, Mich.

[73] Assignee: The Dow Chemical Company, Midland, Mich.

[21] Appl. No.: 408,292

[22] Filed: Aug. 16, 1982

[51] Int. Cl.$^3$ .................... A61K 31/47; C07D 215/34
[52] U.S. Cl. .................................... 424/258; 546/175
[58] Field of Search ....................... 546/175; 424/258

[56] References Cited

U.S. PATENT DOCUMENTS 3,538,099 11/1970 Rohr et al. ................... 546/175

FOREIGN PATENT DOCUMENTS 1087122 10/1967 United Kingdom ............ 546/175

*Primary Examiner*—Paul M. Coughlan, Jr.
*Assistant Examiner*—D. B. Springer

[57] ABSTRACT

Novel 8-quinolinyl carbamates are disclosed possessing anti-bacterial and anti-fungal activity. The compounds show significant activity against gram-negative organisms making them useful in the treatment of urinary tract infections.

20 Claims, No Drawings

8-QUINOLINYL CARBAMATES AND THEIR USE AS URINARY TRACT ANTIMICROBIALS

SUMMARY OF THE INVENTION

The present invention is directed to an antimicrobial compound corresponding to the formula:

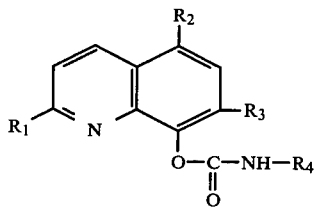

wherein $R_1$ is hydrogen or lower alkyl; $R_2$ is hydrogen, nitro ($-NO_2$) or halo; $R_3$ is hydrogen or halo; and $R_4$ is:

(a)

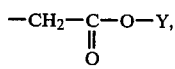

wherein Y is lower alkyl, provided that when Y is ethyl (i.e., $-CH_2CH_3$), at least one of $R_1$, $R_2$ and $R_3$ is substituted as defined above with a moiety other than hydrogen; or (b) $-CH_2CH_2Cl$ (provided that both $R_1$ and $R_3$ are hydrogen and $R_2$ is halo), and pharmaceutically-acceptable salts thereof.

As used herein, the term "lower alkyl" refers to aliphatic, straight or branched chain radicals of from one to about four carbon atoms inclusive; the term "halo" refers to a member selected from the group consisting of fluorine, chlorine, bromine or iodine.

Of the compounds of the present invention those compounds wherein $R_4$ is:

$$-CH_2C-O-Y \quad \text{(II)}$$
$$\underset{O}{\|}$$

(where Y has the meaning previously given) are preferred.

Of the preferred compounds, those compounds wherein $R_1$ is hydrogen and $R_2$ and $R_3$ are the same halo are especially preferred.

Of the preferred compounds, those compounds wherein $R_1$ and $R_3$ are hydrogen and $R_2$ is nitro are also especially preferred.

The compounds corresponding to Formula I typically exhibit antimicrobial activity against a wide variety of bacteria and fungi such as *Escherichia coli, Bacillus subtilis, Klebsiella pneumoniae, Pseudomonas aeruginosa, Proteus mirabilis, Candida albicans,* and *Aspergillus niger,* making them useful in a wide variety of industrial, agricultural and consumer applications. Also, the compounds of this invention typically exhibit significant activity against gram negative bacteria, making them potentially useful in the treatment of urinary tract infections.

DETAILED DESCRIPTION OF THE INVENTION

The various compounds of the present invention (and the starting materials used therein) may be prepared by utilizing materials and methods well-known to the art. See, for example, U.S. Pat. No. 3,362,960; British Pat. No. 1,087,122; Chemical Abstracts 69:10380n (1968); *J. Amer. Chem. Soc.* 84:4899 (1962).

The compounds represented by formula I may be prepared by reacting an appropriately substituted 8-hydroxyquinoline represented by the formula:

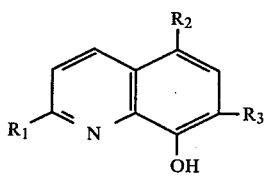

where $R_1$, $R_2$, and $R_3$ have the meaning previously given with about an equimolar amount of an $R_4$-substituted isocyanate represented by the formula:

where $R_4$ has the same meaning as defined above. The reactants are contacted in an aprotic solvent such as methyl ethyl ketone, toluene or tetrahydrofuran in the presence of a minor amount of activating agent such as dibutyltin dilaurate or triethylamine. The reaction is allowed to continue at a controlled temperature (usually from about ambient temperature to about reflux temperature) for a period of time sufficient to obtain the desired product (generally from about 1 to about 48 hours). Following reaction, the desired product is isolated and purified by utilizing conventional techniques such as vacuum evaporation and recrystallization. Pharmaceutically-acceptable salts may then be prepared, if desired, by well-known methodology.

The general reaction conditions outlined above are usually sufficient to obtain the desired product. However, longer or shorter reaction times and different reaction temperatures may, in some instances, be necessary or desirable. Such modifications in the general procedures described herein will be obvious to one skilled in the art. Similarly, other methods for preparing compounds of the present invention are, or will be, obvious to one of ordinary skill in the art.

The following examples are set forth as a means of illustrating the present invention, and are not intended as a limitation thereon.

EXAMPLE 1

Ethyl N-(((5-chloro-8-quinolinyl)oxy)-carbonyl)-glycinate

A mixture of 18.0 grams (g) of 5-chloro-8-hydroxyquinoline, 13.6 g of ethyl isocyanatoacetate and 10 drops of dibutyltin dilaurate in 200 milliliters (ml) of methyl ethyl ketone was heated at reflux temperature with stirring for about 4.5 hours. Following reaction, the solvent was removed by evaporation in vacuo leaving a solid residue which was dissolved in 60 ml of hot toluene and subsequently treated with activated charcoal and filtered. The filtrate was cooled to around 4° C. resulting in the crystallization of an off-white solid which was then recrystallized from carbon tetrachloride to give the desired, ethyl N-(((5-chloro-8-quinolinyl)-oxy)carbonyl)glycinate as a white crystalline solid having a melting point (m.p.) of 101°–103° C.

EXAMPLE 2

Ethyl N-(((5,7-dibromo-8-quinolinyl)oxy)carbonyl)glycinate 5,7-Dibromo-8-hydroxyquinoline (19.7 g), ethyl isocyanatoacetate (13.0 g) and triethylamine (6.58 g) were mixed in 200 ml of toluene and heated at reflux temperature for about 47 hours. The solution was cooled to room temperature and the desired ethyl N-(((5,7-dibromo-8-quinolinyl)oxy)carbonyl)glycinate was obtained as a white, crystalline solid, m.p. 129.5° C. (decomposition).

EXAMPLE 3

Ethyl N-(((2-methyl-8-quinolinyl)oxy)carbonyl)glycinate

A mixture of 15.9 g of 2-methyl-8-hydroxyquinoline, 13.6 g of ethyl isocyanatoacetate and 10 drops of dibutyltin dilaurate in 200 ml of methyl ethyl ketone was heated at reflux temperature for seven hours, after which the solvent was removed by evaporation in vacuo leaving a solid residue. The residue was recrystallized from toluene to give the desired ethyl N-(((2-methyl-8-quinolinyl)oxy)carbonyl)glycinate as light tan crystals, m.p. 118°–120° C.

EXAMPLE 4

Ethyl N-(((5,7-dichloro-8-quinolinyl)oxy)carbonyl)glycinate 5,7-Dichloro-8-hydroxyquinoline (21.4 g), ethyl isocyanatoacetate (21.3 g) and triethylamine (1.0 ml) were mixed together in 400 ml of methyl ethyl ketone and stirred at room temperature for about 42 hours resulting in the precipitation of a white crystalline solid. This solid was removed from the reaction mixture by filtration and was determined to be the desired ethyl N-(((5,7-dichloro-8-quinolinyl)oxy)carbonyl)glycinate, m.p. 119.5° C.

EXAMPLE 5

Ethyl N-(((5-nitro-8-quinolinyl)oxy)carbonyl)glycinate

5-Nitro-8hydroxyquinoline (19.0 g) was added to a solution containing 13.6 g of ethyl isocyanatoacetate in 250 ml of methyl ethyl ketone. This mixture was then stirred at room temperature while triethylamine (1.0 g) was added. Stirring was continued at ambient temperature for about 30 minutes when a crystalline mass precipitated. This crystalline solid was collected by filtration, washed with carbon tetrachloride and subsequently dried leaving the desired ethyl N-(((5-nitro-8-quinolinyl)oxy)carbonyl)glycinate as cream colored crystals, m.p. 121°–122° C.

EXAMPLE 6

5-Chloro-8-quinolinyl N-(2-chloroethyl)carbamate

5-Chloro-8-hydroxyquinoline (35.9 g), 2-chloroethyl isocyanate (21.1 g), and triethylamine (2.02 g) were mixed in 400 ml of methyl ethyl ketone and heted at reflux temperature with stirring for about one hour. The reaction mixture, upon cooling to room temperature, yielded the desired 5-chloro-8-quinolinyl N-(2chloroethyl)carbamate as glistening, cream colored cystals, m.p. 146° C.

Salts of compounds of the present invention may be prepared by techniques known to the art. The following examples are illustrative.

EXAMPLE 7

Ethyl N-(((5-chloro-8quinolinyl)oxy)carbonyl)glycinate methanesulfonic acid salt To a stirred solution of 4.53 g of ethyl N-(((5-chloro-8-quinolinyl)oxy)carbonyl)glycinate (prepared as described in Example 1) in 80 ml of isopropanol was added a solution of 1.56 g methanesulfonic acid in 10 ml of isopropanol. The resulting solution was cooled to about 0° C. to yield a white solid which was isolated and recrystallized from ethanol to give the purified ethyl N-(((5-chloro-8-quinolinyl)oxy)carbonyl)glycinate methanesulfonic acid salt as white fibrous crystals, m.p. 108°–110° C.

EXAMPLE 8

Ethyl N-(((5-chloro-8-quinolinyl)oxy)carbonyl)glycinate hydrochloride salt 5.0 g of ethyl N-(((5-chloro-8-quinolinyl)oxy)carbonyl)glycinate (prepared as described in Example 1) was stirred in 30 ml of 5 N hydrochloric acid at room temperature. A precipitate formed and was collected by filtration and subsequently recrystallized from ethanol to give the desired ethyl N-(((5-chloro-8-quinolinyl)oxy)carbonyl)glycinate hydrochloride salt as pale yellow crystals, m.p. 170° C. (decomposition).

The physical properties of the above examples are summarized in Table 1.

TABLE 1

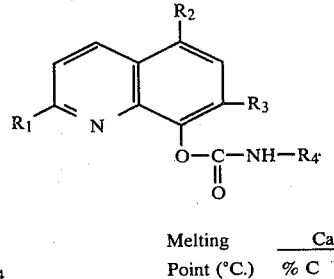

| Compound Example Number | $R_1$ | $R_2$ | $R_3$ | $R_4$ | Melting Point (°C.) | Calculated | | | Found | | |
|---|---|---|---|---|---|---|---|---|---|---|---|
| | | | | | | % C | % H | % N | % C | % H | % N |
| 1 | H | Cl | H | —CH$_2$COCH$_2$CH$_3$ with ‖O | 101°–103° | 54.46 | 4.25 | 9.08 | 54.7 | 4.39 | 9.16 |
| 2 | H | Br | Br | —CH$_2$COCH$_2$CH$_3$ with ‖O | 129.5° (decomp) | 38.91 | 2.80 | 6.48 | 38.9 | 2.85 | 6.52 |

TABLE 1-continued

Structure: quinoline with $R_1$ at 2-position, $R_2$ at 5-position, $R_3$ at 7-position, and O-C(=O)-NH-$R_4$ at 8-position.

| Compound Example Number | $R_1$ | $R_2$ | $R_3$ | $R_4$ | Melting Point (°C.) | Calculated % C | Calculated % H | Calculated % N | Found % C | Found % H | Found % N |
|---|---|---|---|---|---|---|---|---|---|---|---|
| 3 | CH$_3$ | H | H | —CH$_2$COCH$_2$CH$_3$ (with C=O) | 118°–120° | 62.49 | 5.59 | 9.72 | 62.3 | 5.61 | 9.85 |
| 4 | H | Cl | Cl | —CH$_2$COCH$_2$CH$_3$ (with C=O) | 119.5° | 49.00 | 3.53 | 8.17 | 49.0 | 3.71 | 8.32 |
| 5 | H | NO$_2$ | H | —CH$_2$COCH$_2$CH$_3$ (with C=O) | 121°–122° | 52.67 | 4.10 | 13.16 | 52.57 | 4.14 | 13.05 |
| 6 | H | Cl | H | —CH$_2$CH$_2$Cl | 146° | 50.55 | 3.54 | 9.83 | 50.4 | 3.50 | 9.84 |
| 7[a] | H | Cl | H | —CH$_2$COCH$_2$CH$_3$ (with C=O) | 108°–110° | 44.50 | 4.23 | 6.92 | 44.52 | 4.64 | 6.56 |
| 8[b] | H | Cl | H | —CH$_2$COCH$_2$CH$_3$ (with C=O) | 170° (decomp) | 48.71 | 4.09 | 8.12 | 48.7 | 4.24 | 8.32 |

[a] As the methanesulfonic acid salt
[b] As the hydrochloric acid salt

Other compounds useful in the method of treating urinary tract infections described herein which are not encompassed by formula I are:

EXAMPLE 9

Ethyl N-(((8-quinolinyl)oxy)carbonyl)glycinate, m.p. 136.5°–137.5° C.

EXAMPLE 10

5,7-Dichloro-8quinolinyl N-methylcarbamate, m.p. 145°–146° C.

EXAMPLE 11

5,7-Dibromo-8-quinolinyl N-methylcarbamate, m.p. 1980°–200.5° C.

The compounds of the present invention are useful as antimicrobial agents and may be utilized against various bacteria and fungi in a variety of applications. Their effectiveness varies with the concentration of compound employed and the particular organism tested. While not all compounds are effective at similar concentrations against the same organisms, all compounds of the present invention may be utilized as antibacterial agents, antifungal agents or both.

Examples of the bacteria and fungi controlled by effective amounts of one or more of the compounds are Staphylococcus aureus, Salmonella typhosa, Escherichia coli, Proteus mirabilis, Bacillus subtilis, Streptococcus mutans, Enterobacter aerogenes, Ceratocystis ips, and Trichophyton mentagrophytes. As used herein the term "effective amount" refers to that amount of one or more of the compounds needed to exhibit either static or cidal effects on selected organisms. Typically, this amount varies from about 0.5 to about 750 parts per million (ppm) by weight depending upon the particular compound tested and organism treated.

In the treatment of urinary tract infections, the compounds are preferbly administered in the form of a composition comprising the compound in admixture with a pharmaceutically-acceptable carrier, i.e., a carrier which is chemically inert to the active compound and which has no detrimental side effects or toxicity under the conditions of use.

The compositions can be in solid forms such as tablets, capsules, powders, granules or the like, as well as liquid forms such as sterile parenteral suspensions, or orally administered suspensions or solutions. The pharmaceutically-acceptable carriers can include excipients such as surface active dispersing agents, suspending agents, tableting binders, lubricants, flavors and colorants. Suitable excipients are disclosed, for example, in texts such as Remington's Pharmaceutical Sciences, Fourteenth Edition, Mack Publishing Co. (1970).

The antimicrobial activity of the compounds described herein was demonstrated by the following techniques.

EXAMPLE 12

The test compound was added to molten agar as a solution (when conveniently soluble in a solvent such as dimethylformamide) or a suspension forming a mixture having a concentration of 0.05 percent (500 ppm). The mixture was stirred and poured into plates to harden. When hardened, the plates were inoculated with various bacteria and fungi. The bacteria-inoculated plates were incubated at 37° C. for 24 hours, while the fungi-inoculated plates were incubated for about 72–120 hours. Following incubation, the plates were examined for growth or inhibition of the respective organisms.

After the initial readings, compounds showing sufficient activity were re-tested at various concentrations to determine the minimum inhibitory concentration (in ppm) of the compounds of the invention against the various bacteria and fungi tested. The results of these tests are summarized in Table 2.

TABLE 2

-continued

| | | |
|---|---|---|
| Escherichia coli | ATCC 9723 | (Ec 9723) |
| Escherichia coli | ATCC 11229 | (Ec 11229) |
| Escherichia coli | ATCC 25922 | (Ec 25922) |
| Proteus mirabilis | 470/1 | (Pm 470/1) |
| Staphylococcus aureus | ATCC 25923 | (Sa 25923) |

TABLE 3

Minimum Inhibitory Concentrations (ppm)

| Organism[1] | Compound Example Number | | | | | | | | | | |
|---|---|---|---|---|---|---|---|---|---|---|---|
| | 1 | 2 | 3 | 4 | 5 | 6 | 7 | 8 | 9 | 10 | 11 |
| Ea 13048 | 50 | 75 | 250 | 25 | 25 | 500 | 75 | 50 | 100 | 25 | 25 |
| Pa 7700 | 100 | 250 | >1000 | 50 | 100 | 500 | 250 | 100 | 500 | 50 | 100 |
| Pa 10145 | 25 | 25 | 250 | 10 | 25 | NT | 75 | 75 | 50 | 10 | 25 |
| Pa 27853 | 100 | 75 | >1000 | 50 | 75 | 500 | 250 | 100 | 250 | 50 | 100 |
| Pa PRD-10 | 100 | 75 | >1000 | 50 | 50 | 500 | 250 | 100 | 500 | 25 | 100 |
| Kp M-1 | 50 | 50 | 250 | 25 | 25 | 250 | 75 | 50 | 100 | 25 | 25 |
| Kp M-2 | 50 | 25 | 250 | 25 | 25 | 500 | 75 | 50 | 100 | 25 | 25 |
| Kp M-6 | 25 | 25 | 250 | 25 | 25 | 250 | 50 | 25 | 75 | 25 | 25 |
| Kp 23357 | 25 | 250 | 250 | 25 | 10 | 250 | 75 | 50 | 50 | 10 | 25 |
| Sr M-1 | 50 | 250 | 750 | 25 | 50 | 500 | 100 | 75 | 100 | 25 | 50 |
| Ec 4157 | 25 | 25 | 100 | 10 | 25 | 250 | 50 | 25 | 75 | 10 | 25 |
| Ec 9723 | 25 | 25 | 100 | 10 | 25 | 50 | 50 | 25 | 75 | 10 | 25 |
| Ec 11229 | 25 | 25 | 75 | 10 | 25 | 75 | 50 | 25 | 75 | 10 | 25 |
| Ec 25922 | 25 | 25 | 75 | 10 | 10 | 75 | 25 | 25 | 75 | 10 | 25 |
| Pm 470/1 | 50 | 25 | 250 | 10 | 10 | 250 | 75 | 50 | 75 | 10 | 25 |
| Sa 25923 | ≦5 | 25 | 25 | 10 | 25 | <5 | <5 | 10 | 10 | <5 | 25 |

[1]Abbreviations explained in Example 13.

Minimum Inhibitory Concentrations (ppm)

| Compound Example Number | Test Organisms* | | | | | | | |
|---|---|---|---|---|---|---|---|---|
| | Bs | Sm | St | Ca | Cp | Ci | An | Tm |
| 1 | 10 | 100 | 50 | 10 | 10 | 50 | 10 | 10 |
| 2 | 0.5 | 50 | 50 | 50 | 10 | 50 | 50 | 50 |
| 3 | 10 | 500 | 50 | 500 | 500 | 500 | 500 | 500 |
| 4 | 1.0 | 500 | 10 | 10 | 5 | 50 | 10 | 10 |
| 5 | 5 | NI** | 5 | 50 | 50 | 100 | 50 | 50 |
| 7 | 5 | 500 | 10 | 50 | 50 | 50 | 50 | 10 |
| 8 | 1.0 | NI** | 50 | 10 | 10 | 50 | 10 | 10 |
| 9 | 10 | 5 | 50 | 100 | 50 | 100 | 100 | 50 |
| 10 | 0.5 | 10 | 10 | 5 | 5 | 50 | 10 | 50 |

*Bs = Bacillus subtilis
Sm = Streptococcus mutans
St = Salmonella typhosa
Ca = Candida albicans
Cp = Candida pelliculosa
Ci = Ceratocystis ips
An = Aspergillus niger
Tm = Trichophyton mentagrophytes
**NI = No Inhibition at 500 ppm.

EXAMPLE 13

Following a procedure substantially the same as that described in Example 12, the minimum inhibitory concentration for the compounds described herein was determined for various organisms representative of those commonly associated with urinary tract infections.

These results are described in Table 3. The organisms used in this procedure and the abbreviations designated in Table 3 are as follows:

| | | |
|---|---|---|
| Enterobacter aerogenes | ATCC 13048 | (Ea 13048) |
| Pseudomonas aeruginosa | ATCC 7700 | (Pa 7700) |
| Pseudomonas aeruginosa | ATCC 10145 | (Pa 10145) |
| Pseudomonas aeruginosa | ATCC 27853 | (Pa 27853) |
| Pseudomonas aeruginosa | PRD-10 | (Pa PRD-10) |
| Klebsiella pneumoniae | M-1 | (Kp M-1) |
| Klebsiella pneumoniae | M-2 | (Kp M-2) |
| Klebsiella pneumoniae | M-6 | (Kp M-6) |
| Klebsiella pneumoniae | ATCC 23357 | (Kp 23357) |
| Serratia marcescens | M-1 | (Sr M-1) |
| Escherichia coli | ATCC 4157 | (Ec 4157) |

EXAMPLE 14

The urinary tract antimicrobial activity of the compounds described herein was determined by the following procedure.

A sample of the compound being tested was suspended in 0.5 percent methylcellulose and injected intraperitoneally into a mouse at a dosage of 60 milligrams per kilogram of body weight. At about 0.5, 1 and 2 hours after injection, the lower abdomen of the mouse was gently massaged to stimulate urination. The urine was collected and used to saturate ¼ inch filter paper discs which were then dried at room temperature. After drying, the discs were placed on the surface of agar plates seeded with a suspension of *Escherichia coli* (ATCC 25922) or *Staphylococcus aureus* (ATCC 25923). The plates were incubated for 24 hours at 37° C., and then examined for a presence or absence of a zone of inhibition of growth of the organism around the filter paper disc.

The results of this test are provided in Table 4.

TABLE 4[a]

| Compound Example Number | Organism | | | | | |
|---|---|---|---|---|---|---|
| | E. Coli Time (hrs.) | | | S. aureus Time (hrs.) | | |
| | 0.5 | 1 | 2 | 0.5 | 1 | 2 |
| 1 | + | + | + | + | + | + |
| 2 | + | + | + | − | NS | NS |
| 3 | + | +[b] | − | NS | + | − |
| 4 | +[c] | NS | +[c] | + | NS | − |
| 5 | +[c] | +[c] | NS | + | NS | NS |
| 7 | + | + | − | + | + | − |
| 9 | +[c] | +[c] | +[c] | + | + | + |
| 10 | + | NS | NS | + | NS | NS |
| 11 | − | − | − | + | NS | + |

[a]In Table 4, "+" indicates the presence of a zone of inhibition around the disc; "−" indicates the absence of a zone of inhibition around the disc; "NS" indicates no urine sample available at the time specified.
[b]Incomplete inhibition within the zone.
[c]Zone of inhibition present, but with trailing zone ends.

What is claimed is:
1. A compound of the formula:

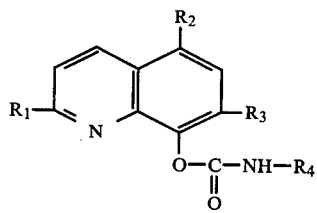

wherein $R_1$ is hydrogen or lower alkyl; $R_2$ is hydrogen, nitro or halo; $R_3$ is hydrogen or halo; and $R_4$ is

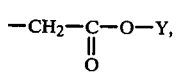

wherein Y is lower alkyl, provided that at least one of $R_1$, $R_2$ and $R_3$ is other than hydrogen; and pharmaceutically-acceptable salts thereof.

2. The compound of claim 1 wherein $R_1$ is hydrogen, $R_2$ and $R_3$ are the same halo, and $R_4$ is

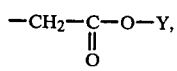

wherein Y is lower alkyl.

3. The compound of claim 1 wherein $R_1$ and $R_3$ are hydrogen, $R_2$ is nitro and $R_4$ is

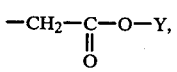

wherein Y is lower alkyl.

4. The compound of claim 1 which is ethyl N-(((5-chloro-8-quinolinyl)oxy)carbonyl)glycinate.

5. The compound of claim 1 which is ethyl N-(((5,7-dibromo-8-quinolinyl)oxy)carbonyl)glycinate.

6. The compound of claim 1 which is ethyl N-(((2-methyl-8-quinolinyl)oxy)carbonyl)glycinate.

7. The compound of claim 1 which is ethyl N-(((5-chloro-8-quinolinyl)oxy)carbonyl)glycinate methanesulfonic acid salt.

8. The compound of claim 1 which is ethyl N-(((5-chloro-8-quinolinyl)oxy)carbonyl)glycinate hydrochloride salt.

9. The compound of claim 2 which is ethyl N-(((5,7-dichloro-8-quinolinyl)oxy)carbonyl)glycinate.

10. The compound of claim 3 which is ethyl N-(((5-nitro-8-quinolinyl)oxy)carbonyl)glycinate.

11. A method of treating urinary tract infections in animals which comprises administering to said animals an effective amount of a compound of the formula:

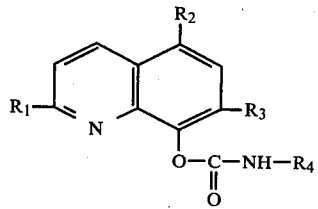

wherein $R_1$ is hydrogen or lower alkyl; $R_2$ is hydrogen, nitro or halo; $R_3$ is hydrogen or halo; and $R_4$ is

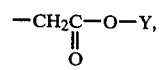

wherein Y is lower alky, provided that when Y is ethyl, at least one of $R_1$, $R_2$ and $R_3$ is other than hydrogen; or a pharmaceutically-acceptable salt thereof.

12. The method of claim 11 wherein the compound administered is ethyl N-(((5-chloro-8-quinolinyl)oxy)carbonyl)glycinate.

13. The method of claim 11 wherein the compound administered is ethyl N-(((5,7-dibromo-8-quinolinyl)oxy)carbonyl)glycinate.

14. The method of claim 11 wherein the compound administered is ethyl N-(((2-methyl-8-quinolinyl)oxy)carbonyl)glycinate.

15. The method of claim 11 wherein the compound administered is ethyl N-(((5-chloro-8-quinolinyl)oxy)carbonyl)glycinate methanesulfonic acid salt.

16. The method of claim 11 wherein the compound administered is ethyl N-(((5,7-dichloro-8-quinolinyl)oxy)carbonyl)glycinate.

17. The method of claim 11 wherein the compound administered is ethyl N-(((5-nitro-8-quinolinyl)oxy)carbonyl)glycinate.

18. A method of treating urinary tract infections in animals which comprises administering to said animals an effective amount of ethyl N-(((8-quinolinyl)oxy)carbonyl)glycinate.

19. A method of treating urinary tract infections in animals which comprises administering to said animals an effective amount of 5,7-dichloro-8-quinolinyl N-methylcarbamate.

20. A method of treating urinary tract infections in animals which comprises administering to said animals an effective amount of 5,7-dibromo-8-quinolinyl N-methylcarbamate.

* * * * *